(12) United States Patent
Rea (10) Patent No.: US 9,180,056 B2
(45) Date of Patent: Nov. 10, 2015

(54) MEDICAL BANDAGES WITH A SKIN ADHESION REDUCING MATERIAL

(75) Inventor: Ryan Michael Rea, Ventura, CA (US)

(73) Assignee: Neural Pathways, LLC, Ventura, CA (US)

( * ) Notice: Subject to any disclaimer, the term of this patent is extended or adjusted under 35 U.S.C. 154(b) by 35 days.

(21) Appl. No.: 13/603,803

(22) Filed: Sep. 5, 2012

(65) Prior Publication Data

US 2013/0060184 A1   Mar. 7, 2013

Related U.S. Application Data

(60) Provisional application No. 61/531,445, filed on Sep. 6, 2011.

(51) Int. Cl.
*A61L 15/58* (2006.01)
*A61F 13/02* (2006.01)

(52) U.S. Cl.
CPC .................. *A61F 13/0246* (2013.01)

(58) Field of Classification Search
USPC ........ 424/447–448; 602/41, 54, 57; D24/189; 604/360; 427/207.1; 156/196
See application file for complete search history.

(56) References Cited

U.S. PATENT DOCUMENTS

| | | | |
|---|---|---|---|
| 4,324,595 A | 4/1982 | Kasprzak | |
| 4,769,028 A * | 9/1988 | Hoffmann et al. | 424/443 |
| 4,808,172 A * | 2/1989 | Murata | 604/306 |
| 4,834,979 A | 5/1989 | Gale | |
| 4,858,604 A * | 8/1989 | Konishi | 602/57 |
| 4,867,981 A | 9/1989 | Grof | |
| 4,909,243 A * | 3/1990 | Frank et al. | 602/58 |
| 5,271,940 A * | 12/1993 | Cleary et al. | 424/448 |
| 5,336,207 A | 8/1994 | Norcia | |
| 5,846,559 A * | 12/1998 | Hopp | 424/448 |
| 7,238,849 B2 * | 7/2007 | Goldberg et al. | 602/48 |
| 7,396,976 B2 | 7/2008 | Hurwitz et al. | |
| 2004/0002676 A1 | 1/2004 | Siegwart et al. | |
| 2005/0066965 A1 | 3/2005 | Cronk et al. | |
| 2007/0166357 A1 | 7/2007 | Shaffer et al. | |
| 2008/0269661 A1 * | 10/2008 | Hurwitz et al. | 602/57 |
| 2009/0036849 A1 * | 2/2009 | Gustafson et al. | 604/360 |
| 2012/0123220 A1 | 5/2012 | Iyer et al. | |

OTHER PUBLICATIONS

International Search Report and Written Opinion for PCT/US2012/053755, dated Nov. 2, 2012.
Ezgi, Ms 304 2.Quiz, Blog describing how bandages are made. http://ezgitasdemir.blogspot.com/2008/10/bandage.html (2008).

* cited by examiner

*Primary Examiner* — Ophelia A Hawthorne
(74) *Attorney, Agent, or Firm* — Hansen IP Law PLLC (57) ABSTRACT

A bandage that facilitates the removal of the bandage from the skin is shown and described. The bandage has a selectively releasable adhesion reducing material contained in structures such as a selectively rupturable reservoir or a selectively deformable synthetic or natural matrix. When the adhesion reducing material is released from the reservoir, it contacts the bandage's skin adhesive and reduces its adhesion to the skin.

16 Claims, 8 Drawing Sheets

MEDICAL BANDAGES WITH A SKIN ADHESION REDUCING MATERIAL

CROSS-REFERENCE TO RELATED APPLICATIONS

This application claims the benefit of U.S. Provisional Patent Application No. 61/531,445, filed on Sep. 6, 2011, the entirety of which is hereby incorporated by reference.

FIELD

The present disclosure relates to bandages, and more particularly, to bandages that include a selectively releasable adhesion reducing material for decreasing the adhesive forces between a bandage and a user's skin and the trauma associated with removing the bandage.

BACKGROUND

Historically, sterile latex free medical strip bandages have incorporated a liquid absorbent pad comprising a non-stick cotton fabric, plastic or polymer fabric and/or silicon fabric covers wounds, a backing comprising paper, vinyl, cloth and/or plastic "sheer" flexible zinc oxide, with a skin adhesive such as a hypoallergenic acrylic adhesive for affixing the bandage to the patient's skin to hold the absorbent pad in proper position over the wound. Moreover, most major strip bandage manufacturers such as Band-Aid® use breathable porous or perforated flexible adhesive materials in their bandage strips. Breathable adhesive bandage strips provide greater comfort to patients by allowing airflow to the skin. Furthermore, conventional strip bandages may be waterproof and offered in a variety of different shapes and sizes depending upon the size and location of the wound on the patient's body. For example, depending upon the size and the location of the wound on the patient's body a strip bandage may be oblong, rectangular, round, triangular, square (etc.) in shape. Bandage sizes typically range from ⅝ in×2¼ in (1.5 cm×5.7 cm), ¾ in×3 in (1.9 cm×7.6 cm), 1 in×3 in (2.5 cm×7.6 cm), ⅝ in×2¼ in (1.5 cm×5.7 cm), ¾ in×3 in (1.9 cm×7.6 cm) for skin lesions and minor skin scraps on the body to 1½ in×3 in (3.8 cm×7.6 cm) and 1½ in×2³⁄₁₆ in (3.8 cm×5.5 cm) for skin lesions and minor skin scraps on the knuckles and fingertips. Conventional strip bandages have also been aesthetically improved by superimposing cartoon characters onto the bandages, making bandages glow in the dark, matching bandage colors to patient skin colors and by clear or "see through" bandage strip designs.

Regardless of modern medical strip bandage technology advancements, the problems associated with removing conventional adhesive strip bandages have not been solved and continue to be of paramount importance to the industry. This is because removing adhesive bandage strips is typically painful, particularly for children (pediatric) and the elderly (geriatric), and may cause body effacement by removing the patient's hair, and/or causing skin irritations, skin trauma and even skin lesions. According to one report by 3M, "1.5 million patients in U.S. health care facilities receive skin injuries caused by bandage removal each year." Presently, doctors often advise patients to lay in warm bath water and wait for the water to loosen up strip bandages' adhesive properties prior to removal. Moreover, an entire strip bandage adhesive removal aftermarket product industry has developed around decreasing patient pain, body effacement, and skin damage such as Smith & Nephew's Uni-Solve Adhesive Remover. Nevertheless, such currently available aftermarket products are inconvenient and require the bandage wearer to separately purchase and apply an adhesive remover to a bandage affixed to the skin. One approach has been developed in which bandage backings are provided with rupturable pockets that include an adhesion reducing material. However this approach may preclude the use of breathable or otherwise permeable backings and can cause undesirable leakage.

As a result, a need has developed for a bandage that addresses the foregoing issues.

BRIEF DESCRIPTION OF THE FIGURES

Like reference numerals refer to like parts in the figures.

DETAILED DESCRIPTION

The present disclosure relates to a medical bandage device that includes a selectively releasable adhesion reducing material. The adhesion reducing material is capable of reducing the adhesive forces between the wearer's skin and the bandage, thereby reducing pain and body effacement during removal. In certain examples, the adhesion reducing material is provided in one or more self-contained selectively rupturable reservoirs attached to a bandage backing. In other examples, one or more adhesion reducing material matrices impregnated with the adhesion reducing material are attached a bandage backing layer and are selectively deformable to release the material.

The adhesion reducing material is preferably a liquid or semi-solid material. Suitable adhesion reducing materials include water, plant extracts, petroleum extracts, and animal extracts. Exemplary plant extracts include olive oil, safflower oil, cotton seed oil, peanut oil, soybean oil, castor oil, sesame oil, aloe vera and eucalyptus oil. Exemplary animal extracts include fatty acids such as those found in emu oil. Exemplary petroleum extracts include petrolatum (petroleum jelly) and mineral oil. One exemplary petrolatum is White Petrolatum USP skin protectant, which is a semi-solid mixture of hydrocarbons that is capable of breaking down certain off-the-shelf adhesives, such as cyanoacrylates, which are used in traditional breathable bandages.

Other suitable adhesion reducing materials include many off-the-shelf medical adhesive solvents designed for removing medical bandages. The active ingredients for most of these adhesive solvents are Dipropylene Glycol Methyl Ether, Isoparaffin C10-C11, and Isopropyl Alcohol.

In certain examples described herein, the adhesion reducing material is provided in at least one selectively rupturable reservoir that is attached to the bandage backing layer such that when the user ruptures the reservoir, the adhesion reducing material is released from the reservoir. In this context the term "released" refers not only to examples in which the adhesion reducing material begins to flow freely once the reservoir is ruptured, but also those in which the adhesion reducing material becomes accessible to the user and available for the user to contact and spread over desired locations on the bandage. In preferred embodiments, the bandage is breathable, microporous, channeled or in some other way permeable to the adhesion reducing material so that the adhesion reducing material can flow over or be applied to the backside of the bandage backing layer upon release and then migrate to the opposite side of the backing to make contact with the skin adhesive and diminish its adhesive forces with the bandage wearer's skin.

As will be discussed further herein, in certain examples, the selectively rupturable reservoir includes a housing and a sealing membrane. In certain cases, the selective rupturing comprises rupturing the housing. In other cases, the selective rupturing comprises rupturing the sealing membrane. In other cases, both the housing and sealing membrane may be ruptured. In certain examples, the adhesion reducing material is completely self-contained in the selectively rupturable reservoir such that the bandage backing itself does not form part of the reservoir.

In other examples, the medical bandages described herein include an adhesion reducing material layer or section, in the form of a synthetic or natural matrix (e.g., a film, foam, or gauze) that is distinct from the backing itself and capable of absorbing and retaining the adhesion reducing material until deformed by a user to cause the material to be released.

Figure 1:
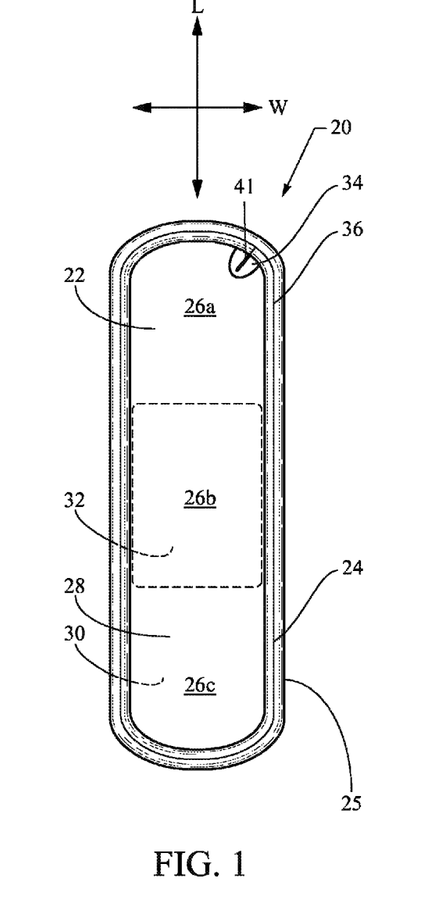
FIG. 1 is a top plan view of a first embodiment of a bandage with an adhesion reducing material contained in a selectively rupturable reservoir attached to the bandage backing.

Referring to FIG. 1, a first example of a medical bandage 20 with a selectively releasable adhesion reducing material (not visible) is depicted. Medical bandage 20 may be used in a wide variety of applications and includes adhesive strip bandages, adhesive gauze, adhesive tapes, adhesive nasal dilators, and butterfly wound closing bandages.

The backing layer 22 includes two surfaces 28 (facing the viewer in FIG. 1) and 30 (facing away from the viewer in FIG. 1). Bandage 20 includes an absorbent pad region 26*b* and two skin adhesive regions 26*a* and 26*c*. The regions define particular locations along the length axis direction L and width axis direction W of bandage 20. The absorbent pad region 26*b* corresponds to the locations along the length L and width W axes where an absorbent pad 32 is present on lower surface 30 of backing layer 22. Skin adhesive regions 26*a* and 26*c* correspond to locations along the length L and width W axes where a skin adhesive is found on the lower surface 30 of backing layer 22. The two skin adhesive regions 26*a* and 26*c* are spaced apart from one another along the bandage length axis direction L such that the absorbent pad region 26*b* is located between first and second skin adhesive regions 26*a* and 26*c*.

Backing layer 22 may be comprised of a number of materials, including paper, woven or non-woven cloths, ETS (a special fabric that is elastic in only one direction) or plastic films. Composites of polymeric films with woven or non-woven cloths may also be used. Exemplary plastic films include polyethylene, polyurethane, polyolefin, EVA (ethylene vinyl acetate), Coflex (a latex free elastic material commonly used for bandage backings) and polyvinyl chloride films. In preferred examples, backing layer 22 is permeable to an adhesion reducing material so that the material may migrate from one side of the backing to the other. Many bandage backings are breathable to facilitate wound healing and water vapor transport from the user's skin which provides a pathway for such migration.

Lower surface 30 of backing layer 22 includes a skin adhesive coating that defines length L and width W dimensions corresponding to skin adhesive regions 26*a* and 26*c*. The skin adhesive coating preferably comprises a skin compatible, medical grade pressure sensitive adhesive. Suitable adhesives include acrylic-based, dextrin based, and urethane based adhesives as well as natural and synthetic elastomers. Suitable examples include amorphous polyolefins (e.g., including amorphous polypropylene), Kraton® Brand synthetic elastomers, and natural rubber. Other exemplary skin adhesives include cyanoacrylates, hydrocolloid adhesives, hydrogel adhesives, and soft silicone adhesives. The skin adhesive coating may also include additives such as tackifiers, antioxidants, processing oils, and the like. The adhesive may be applied to backing surface 30 in any desired manner, including without limitation, spraying, screen printing, or slot die coating. In certain examples, typical skin adhesive coating weights range from about 20 grams/m$^2$ to about 100 gram/m$^2$.

Lower side 30 of backing layer 22 is attached to an absorbent pad 32 within absorbent pad region 26*b*. During normal use, the absorbent pad 32 contacts a local skin trauma such as a wound, scrape, abrasion, laceration, etc. on the wearer's body, while the regions 26*a* and 26*c* on backing side 30 contact the wearer's skin, preferably without also contacting the local skin trauma. Suitable absorbent pads include cotton gauzes, and/or combinations of cotton and/or gauze with plastic films, such as those described as being suitable for backing layer 22, above. In those adhesively affixed medical bandages or devices that are not used for wound care or protecting skin trauma areas, the absorbent pad 32 may be excluded.

A selectively rupturable reservoir 24 is disposed on upper surface 28 of backing layer 22. Selectively rupturable reservoir 24 includes a housing 25 that projects toward the viewer in a direction away from bandage backing layer surface 28

(i.e., orthogonally to the L and W axes in FIG. 1). Selectively rupturable reservoir 24 also includes a sealing membrane (not visible in FIG. 1) that is disposed on the upper surface 28 of backing layer 22. The housing 25 and the sealing member are configured to create an enclosed space that contains an adhesion reducing material of the type described previously. The sealing membrane is preferably a thin film that is impermeable to the adhesion reducing material. Suitable sealing membrane materials include thin, flexible polyethylene materials such as LDPE materials. Commercially available LDPE films are often used as membrane, release liners, laminates, etc. and are sometimes supplied with a layer of release coating, such as in the case of siliconized LDPEs or other with layers of other adhesives. Films suitable as sealing membrane materials include LF 444 LDPE, OPTILiner®, and SUPRALiner® release liners, supplied by Saint-Gobain Performance Plastics. Other suitable release liners include Silthene® Silicone coated polyethylene and SilProp® Silicone coated polypropylene, supplied by 3M as well as 3M Easy Release Liner Unapplied 33, 3M Non-Silicone Release Liners 4935, 3M Secondary Liner-Non-Silicone 5932, 3M Secondary Liner—Non-Silicone 5932, 3M Silicone Release Liners 4988, 3M Silicone Release Liners 4996, and 3M Silicone Release Liners 4999. Other suitable films include polystyrene, polyethylene terephthalate, polyester, polyurethane, Mylar, Melinex, Hostaphan, silicone films, and polyolefins.

In FIG. 1, the selectively rupturable reservoir 24 is a single reservoir having a profile (when viewed in top plan view) which corresponds substantially to the profile of the outer edge of the bandage 20. As will be seen in subsequent examples, a wide variety of top plan view profiles may be used, and the one depicted in FIG. 1 is merely exemplary. The selectively rupturable reservoir 24 is preferably self-contained, i.e., the bandage backing does not form part of the reservoir 24 or its internal enclosure, to better ensure that the adhesion reducing material is not prematurely released or subject to leakage. A cross-sectional view of the housing 25 and the sealing membrane will be described below with reference to FIGS. 10 and 13.

The housing 25 is preferably comprised of a generally rigid plastic material that can be ruptured by pulling a pull tab 34 attached to a string 41 that engages the housing 25. Housing 25 may also include one or more score lines 36, comprising a thinned area of housing 25 that facilitates rupturing at a defined location. Suitable housing plastics include polyethylenes such as low density polyethylene (LDPE), linear low density polyethylene (LLDPE), medium density polyethylene (MDPE), high density polyethylene (HDPE), ultra high molecular weight polyethylene (UHMWPE), thermosoftening plastics, silicones, and polyesters. One suitable LDPE material is a R108000 supplied by Saint-Gobain Performance Plastics.

The housing 25 is preferably sized to accommodate a desired amount of adhesion reducing material. In certain examples, the amount of adhesion reducing material corresponds to a selected volume of the material divided by the surface area of the backing side 30 lying within the skin adhesive regions 26a and 26c, i.e., the area of the upper surface 28 of backing layer 22 which lies over skin adhesive applied to lower surface 30 of backing layer 22. In certain examples, the volume of adhesion reducing material in selectively rupturable reservoir 24 per unit surface area is preferably at least about 1.2 µl/cm², more preferably at least about 1.8 µl/cm², and still more preferably at least about 2.0 µl/cm². At the same time or in other examples, the volume per unit surface area is preferably not more than about 4.6 µl/cm², more preferably not more than about 3.4 µl/cm², and still more preferably not more than about 2.5 µl/cm². In one example, the volume of adhesion reducing material per unit surface area of backing side 30 in the skin adhesive regions 26a and 26c is about 2.3 µl/cm². In those examples using multiple reservoirs (e.g., as shown in FIGS. 4-6, 7 and 8), the total amount of desired adhesion reducing material per unit of surface area is preferably evenly allocated among the multiple reservoirs.

The pull string 41 attached to pull tab 34 may be embedded in the housing 25 material or otherwise affixed to an internal surface of the housing 25 (such as by adhesively bonding the string 41 to an inner surface of the housing 25). Pull tab 34 is sized for gripping by a bandage wearer. Pull tab 34 may be formed from a fabric, plastic or any other sturdy, grippable material. A pull string may also be embedded in the housing proximate score line 36 (if provided).

A method of using the removing bandage 20 from a wearer's skin will now be described. Bandage 20 is applied to the wearer's skin with absorbent pad 32 in contact with a skin trauma such as a wound, abrasion, rash, laceration, ulcer, etc. The skin adhesive on lower surface 30 of backing layer 22 (which lies within the boundaries of skin adhesive regions 26a and 26c) is adhered to the wearer's skin on either side of the skin trauma. After a period of use (e.g., one day, two days, one week, two weeks, etc.) the wearer may desire to remove the bandage 20 from his or her skin. At that point, the wearer grips pull tab 34 and pulls it to rupture housing 25, thereby exposing the adhesion reducing material contained in the selectively rupturable reservoir 24 and making it accessible to the wearer. In certain cases, the viscosity of the adhesive reducing material will cause the material to flow over upper surface 28 of backing layer 22 quickly after the housing 25 is ruptured. In other cases, and depending especially on the viscosity of the adhesion reducing material, the wearer may need or want to manually spread the adhesion reducing material across the upper surface 28 of backing layer 22 in order to contact a desired amount of the surface area of the backing layer 22 surface 28. Even in those cases where the adhesion reducing material tends to flow out of the ruptured housing 25, the user may wish to spread it across the portion of the upper surface 28 of the backing layer 22 that lies within the skin adhesive regions 26a and 26c to maximize the area of contact between the skin adhesive and the adhesion reducing material. Once in contact with the upper surface 28 of backing layer 22, the adhesion reducing material preferably migrates through the backing layer 22 from upper surface 28 to lower surface 30 to contact the skin adhesive and diminish the adhesive forces between the backing layer 22 and the wearer's skin. The wearer can then grip and peel the backing layer 22 from the skin with reduced pain and body effacement than would otherwise occur without the adhesion reducing material.

Figure 2:
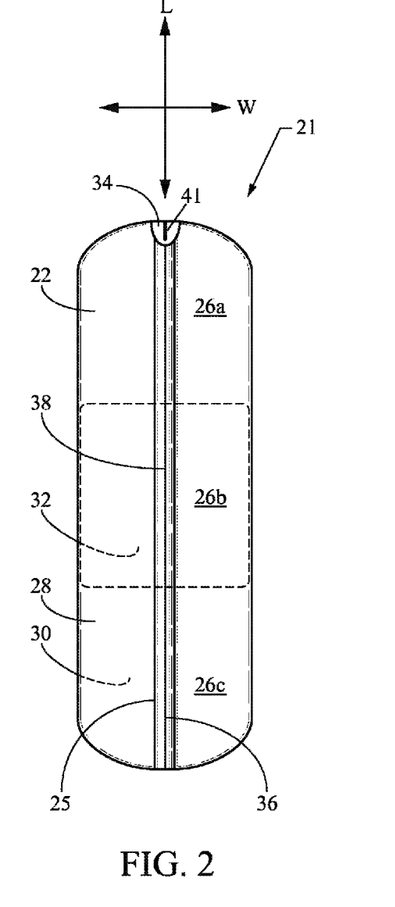
FIG. 2 is a top plan view of a second embodiment of a bandage with an adhesion reducing material contained in a selectively rupturable reservoir attached to the bandage backing.

Referring to FIG. 2, another example of a bandage comprising a selectively releasable adhesion reducing material is depicted. Like the bandage 20 of FIG. 1, bandage 21 of FIG. 2 includes a selectively rupturable reservoir 38 affixed to backing layer 22 surface 28 of bandage 21. The only significant difference between the bandage 21 of FIG. 2 and that of FIG. 1 is in the profile of the selectively rupturable reservoir 38. Selectively rupturable reservoir 38 extends only along the length axis direction L of bandage 20. Pull tab 34 is provided and is attached to a string 41 or fabric (not shown) that engages the reservoir housing 25 such that when the user pulls the pull tab 34, the reservoir housing 25 ruptures. In the case of bandage 20, the selectively rupturable reservoir 38 runs along the longitudinal midline of the backing layer 22 along essentially the entire length of bandage 21 such that the reservoir 38 crosses the absorbent pad region 26b and well as the skin adhesive regions 26a and 26c. In certain examples, the amount of the adhesion reducing fluid contained in the selectively rupturable reservoir 38 is the same per unit surface area of the upper surface 28 of backing layer 22 lying in the first skin adhesive region 26a and second skin adhesive region 26c as described previously with respect to FIG. 1.

Figure 3:
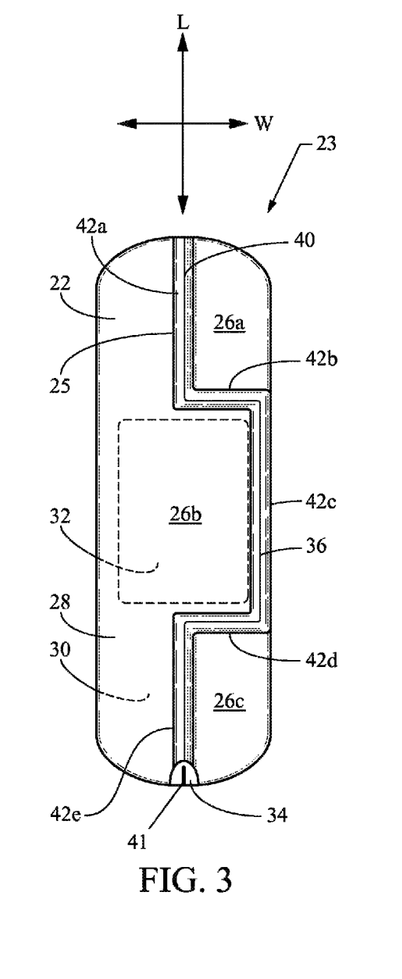
FIG. 3 is a top plan view of a third embodiment of a bandage with an adhesion reducing material contained in a selectively rupturable reservoir attached to the bandage backing.

Referring to FIG. 3, a third example of a bandage with a selectively releasable adhesion reducing material is depicted. Bandage 23 is similar to bandages 20 and 21, except as to the top plan view profile of the selectively rupturable reservoir 40. Selectively rupturable reservoir 40 comprises a plurality of linear segments, 42a, 42b, 42c, 42d, and 42e. The plurality of linear segments comprises a first subplurality of linear segments 42a, and 42e which extend along the longitudinal midline of the bandage backing layer 22 in the direction of the backing length axis L. A second subplurality of linear selectively rupturable reservoir segments 42b and 42d extends along the direction of the backing width axis W, starting from a point at the longitudinal midline of the bandage 23 and extending to a point proximate the width-wise edge of the bandage 23. Segment 42c extends along the length axis direction L but is positioned so as to lie outside the absorbent pad region 26b (i.e., the portion of the backing layer 22 lying immediately above absorbent pad 32).

In the example of FIG. 3, the first and second skin adhesive regions 26a and 26c are connected by two thin backing regions between which the absorbent pad 32 lies. Pull tab 34 and string 41 are again provided to allow a user to selectively rupture the selectively rupturable reservoir 40 in the same manner described previously with respect to FIGS. 1 and 2. The pull tab 34 and string 41 are preferably configured so that the wearer can rupture each linear segment 42a-42e of the selectively rupturable reservoir 40. The reservoir 40 has the same components (a housing and sealing membrane) and cross-sectional profile as the corresponding reservoirs 24 and 38 of FIGS. 1 and 3. The cross-sections will be illustrated and described below with reference to FIGS. 10 and 13. In certain examples, the amount of the adhesion reducing fluid contained in the selectively rupturable reservoir 40 is the same per unit surface area of the upper surface 28 of backing layer 22 lying in the first skin adhesive region 26a and second skin adhesive region 26c as described previously with respect to FIG. 1.

Figure 4:
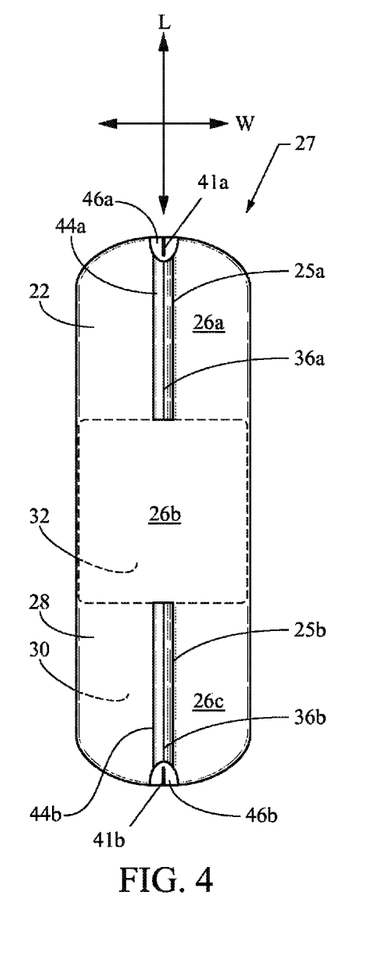
FIG. 4 is a top plan view of a fourth embodiment of a bandage with an adhesion reducing material contained in two selectively rupturable reservoirs attached to the bandage backing.

Referring to FIG. 4, a fourth example of a bandage comprising a selectively releasable adhesion reducing material is depicted. In the example of FIG. 4, bandage 27 comprises two selectively rupturable reservoirs 44a and 44b. Each selectively rupturable reservoir 44a and 44b includes a corresponding one of housing 25a and 25b and a corresponding sealing membrane (not shown) attached to the backing. Each selectively rupturable reservoir 44a and 44b may also include a corresponding score line 36a and 36b to facilitate rupturing of the corresponding hosing 25a and 25b.

Selectively rupturable reservoir 44a is linear in top plan view profile and extends along the direction of the length axis L of the bandage backing layer 22. The reservoir 44a is positioned substantially at the longitudinal midline of bandage backing layer 22. Pull tab 46a and a corresponding string 41a are provided to allow the wearer to selectively rupture reservoir 44a along its length.

Selectively rupturable reservoir 44b is also linear in profile and extends along the length axis direction L of the bandage backing layer 22. The reservoir 44b is also positioned substantially at the longitudinal midline of backing layer 22. Pull tab 46b and a corresponding string 41b are provided to allow the wearer to selectively rupture reservoir 44b. The reservoirs 44a and 44b are spaced apart from one another in the length axis direction L of the bandage. Reservoir 44a is located within the first skin adhesive region 26a of bandage 27, and reservoir 44b is located within the second skin adhesive region 26c of bandage 27. The absorbent pad region 26b of the bandage backing layer 22 lies between the first and second selectively rupturable reservoirs 44a and 44b. The interiors of reservoirs 44a and 44b are not in fluid communication with one another. The reservoirs 44a and 44b are preferably constructed in the same fashion as the reservoirs 24, 38, and 40 of FIGS. 1-3. The reservoir profile and configuration of bandage 27 allows the wearer to selectively and individually reduce the adhesion of one of the skin adhesive regions 26a and 26c by pulling the tab of the respective reservoir and allowing the adhesion reducing material to flow over the backing layer 22 and/or by spreading the adhesion reducing material over the backing layer 22 so that it migrates through the portion of backing layer 22 lying within which ever region 26a or 26c is selected and makes contact with that region's skin adhesive. In certain examples, the total amount of the adhesion reducing fluid contained in the selectively rupturable reservoirs 44a and 44b is the same per unit surface area of the upper surface 28 of backing layer 22 lying in the first skin adhesive region 26a and second skin adhesive region 26c as described previously with respect to FIG. 1. The adhesion reducing material may preferably be distributed evenly between reservoirs 44a and 44b.

Figure 5:
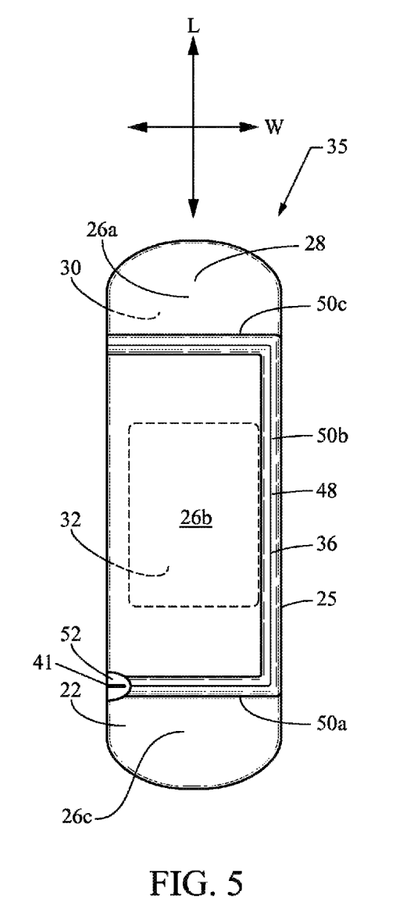
FIG. 5 is a top plan view of a fifth embodiment of a bandage with an adhesion reducing material contained in a selectively rupturable reservoir attached to the bandage backing.

Referring to FIG. 5, a fifth example of a bandage comprising selectively releasable adhesion reducing material is depicted. In the example of FIG. 5, bandage 35 comprises a single selectively rupturable reservoir 48 comprising a plurality of linear segments 50a, 50b, and 50c. Linear segments 50a and 50c comprise a plurality of linear segments extending along the width axis direction W of the bandage backing layer 22. Selectively rupturable reservoir segment 50b connects segments 50a and 50c and extends along the length axis direction L of the bandage backing layer 22. Bandage backing layer 22 has two backing strips that extend in the length axis direction L alongside the absorbent pad region 26b, and segment 50b extends through one of the backing strips while still laying outside of the absorbent pad region 26b (i.e., the segment 50b does not lie above the absorbent pad 32).

Selectively rupturable reservoir segments 50a and 50c are respectively located in skin adhesive regions 26a and 26c of backing layer 22 and are also connected to corresponding ends of segment 50b. The interiors of the selectively rupturable reservoir segments 50a-50c are in fluid communication with one another. Pull tab 52 is provided and is preferably connected to a string 41 that allows the user to rupture the housing 25 of selectively rupturable reservoir 48 along each of its segments 50a-50c. The selectively rupturable reservoir 48 is preferably constructed in the same manner as the reservoirs 24, 38, 44a, and 44b of FIGS. 1-4. In certain examples, the amount of the adhesion reducing fluid contained in the selectively rupturable reservoir 48 is the same per unit surface area of the upper surface 28 of backing layer 22 lying in the first skin adhesive region 26a and second skin adhesive region 26c as described previously with respect to FIG. 1.

Figure 6:
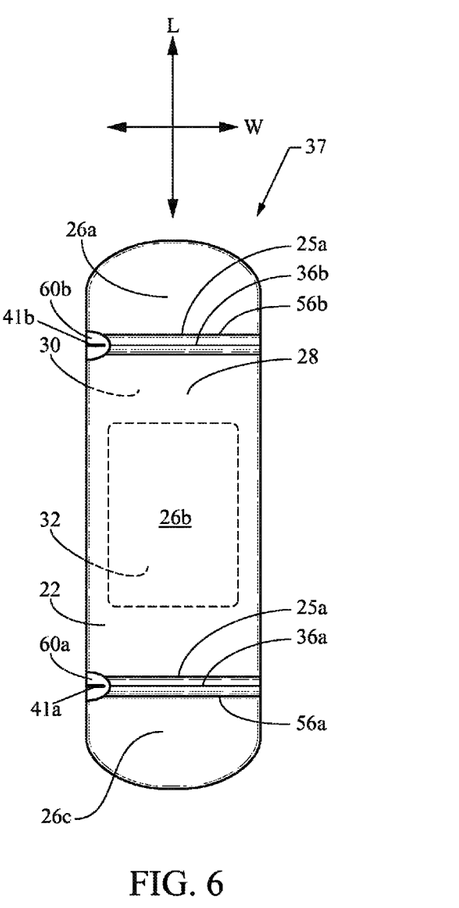
FIG. 6 is a top plan view of a sixth embodiment of a bandage with an adhesion reducing material contained in two selectively rupturable reservoirs attached to the bandage backing.

Referring to FIG. 6, a sixth example of a bandage comprising a selectively releasable adhesion reducing material is depicted. Bandage 37 comprises two selectively rupturable reservoirs 56a and 56b, each of which extends along the width axis direction W of the bandage backing layer 22. Each selectively rupturable reservoir 56a and 56b comprises a corresponding selectively rupturable housing 25a and 25b and a corresponding sealing member (not shown) attached to the upper surface 28 of the backing layer 22. The two selectively rupturable reservoirs 56a and 56b are spaced apart from one another in the length axis direction L of bandage backing layer 22, and their respective interiors are not in fluid communication with one another. Pull tab 60a is connected to a string 41a and may be used to selectively rupture the housing 25a of reservoir 56a. Pull tab 60b is similarly provided with a string 41b for selectively rupturing reservoir 56b. Pull tab 60b is similarly provided with a string (not shown) for selectively rupturing reservoir 56b. As with bandage 27 of FIG. 4, a wearer can selectively reduce the adhesive forces of either bandage skin adhesive region 26a or 26c towards the wearer's skin by rupturing the corresponding selectively rupturable reservoir 56a or 56b. The selectively rupturable reservoirs are preferably constructed in the same manner as the reservoirs 24, 38, 44a, 44b, and 48 of FIGS. 1-5.

A method of making the bandages of FIGS. 1-6 will now be described. In accordance with a first exemplary method, sheets of material used to form backing layer 22 are provided and are coated with a skin adhesive on one side (the side corresponding to lower surface 30 of backing layer 22). The backing layer material is then cut into strips and the absorbent material used to form absorbent pads 32 is cut into strips. Using standard bandage making machinery, the absorbent pad material strips are adhesively adhered to a central portion of the strips of backing layer 22 material such that there is a portion of backing on either side of the absorbent pad strips. The backing portions on either side of the absorbent pad strips will eventually comprise the first and second skin adhesive regions 26a and 26c of the finished bandages. In certain examples, form fill seal equipment or equivalent tooling is used to fill and seal the reservoirs which are formed from the materials described above for housing 25 and the sealing membrane.

Figure 10:
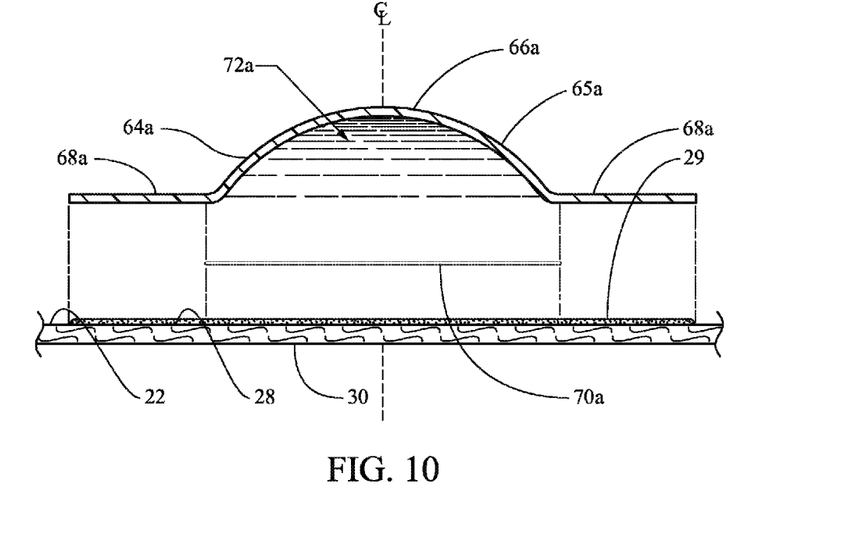
FIG. 10 is an exploded, side cross-sectional view of an embodiment of one of the selectively rupturable reservoirs of the bandage of FIG. 7.
Figure 11:
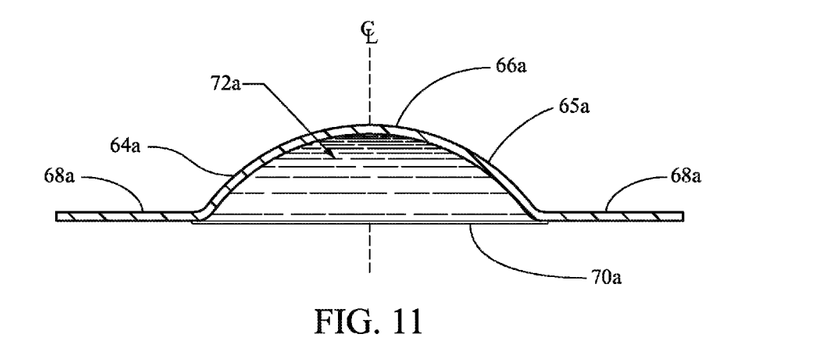
FIG. 11 is a side cross-sectional view of the reservoir of FIG. 10 in sealed configuration.
Figure 13:
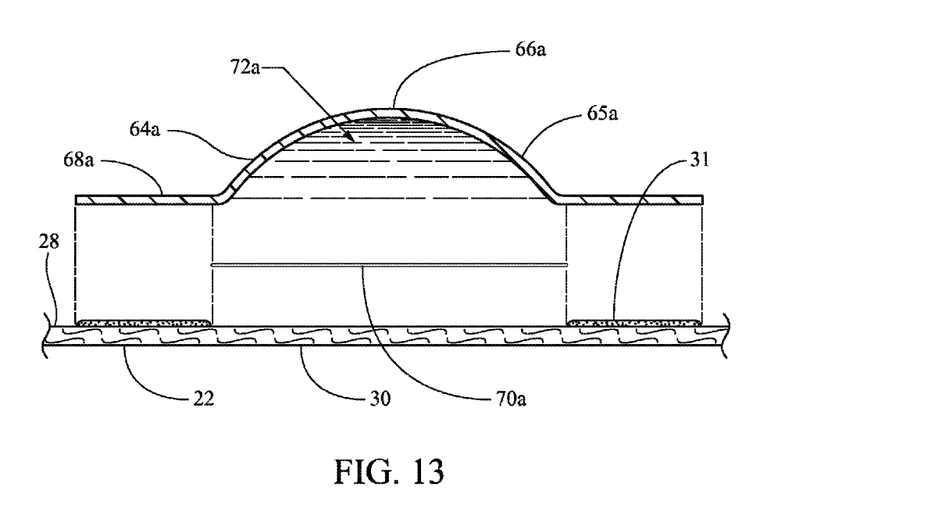
FIG. 13 is an exploded side cross-sectional view of an alternate embodiment of one of the selectively rupturable reservoirs of the bandage of FIG. 7.

The material used to form the housing 25 of the selectively rupturable reservoirs (e.g., an LDPE material used to form the housings of reservoirs 24, 38, 40, 44a, 44b, 48, 56, 58) is shaped using heat (e.g., heat rollers that form dimples of desired dimensions) and/or pressure and cut to create a cross-sectional profile such as that of housing 65a in FIGS. 10 and 11 and the desired top plan view profile (e.g., one of the profiles in FIGS. 1-6). Thus, in the case of reservoirs 24, 38, 40, 44a, 44b, 48, 56, and 58, each housing includes a central domed portion and two side flanges. The central domed portion corresponds to reference numeral 66a in FIGS. 10 and 13 and has flanges on either side. In FIGS. 10 and 13 the flanges are shown as a single flange 68a because FIG. 10 is used to illustrate a circular reservoir (as discussed below) In the case of the reservoirs of FIGS. 1-6, the reservoir top plan view profile is not circular, so each housing 25 would include two flanges on either side of a central domed portion when viewed in cross-section.

The housings 25 are then filled with the adhesion reducing material, and strips of the sealing membrane material are placed over the open face of the housing such that the outer periphery of the sealing strips is located inward of the outermost part of the flanges. This configuration allows the flanges to directly attach to the backing and sandwich the sealing membrane periphery between the flanges and the backing.

The strips of backing material are then coated with a housing adhesive in the desired pattern, and the housing, sealing membrane, and backing strips are assembled together such that the housing is adhesively attached to the backing strips and a portion of the periphery of the sealing membrane is sandwiched between the periphery of the housing and the bandage backing, as will be discussed further below with reference to FIGS. 10-13. Once the housings, backing strips, and sealing membranes are thusly assembled, the assembly can be cut to the desired shape and size to yield the bandage. In preferred examples, one or more release liners with a release coating will be placed over the skin adhesive to protect it prior to use, and the bandages will be packaged and sterilized using known techniques. The packaging and sterilization techniques are preferably selected to maintain the integrity of the reservoirs and the adhesion reducing material.

In accordance with another method of making the bandages of FIGS. 1-6, manufacturing, the strips of sealing membrane material may be supplied as a bulk double-sided adhesive film with adhesive coatings on both sides. The double sided adhesive film would then be applied to the side of the backing material strips that is opposite the side on which the absorbent pad material strips are disposed. Depending on the particular selectively rupturable reservoir top plan view profile, it may be desirable or necessary to cut the double sided adhesive film into a desired shape before placing it on the backing material strips. Once the double sided adhesive film is attached to the backing, the backing can be applied to the liquid filled housings to seal the adhesion reducing material within the enclosure defined by the housings and the sealing membrane material (i.e., the double-sided adhesive film). The housing/film/backing/absorbent pad strips can be cut to the desired shape of the finished bandage. Suitable double-sided adhesive films include double sided adhesive tapes supplied by 3M. The use of such double-sided adhesive films avoids the need for a separate step to apply an adhesive to the backing.

Figure 7:
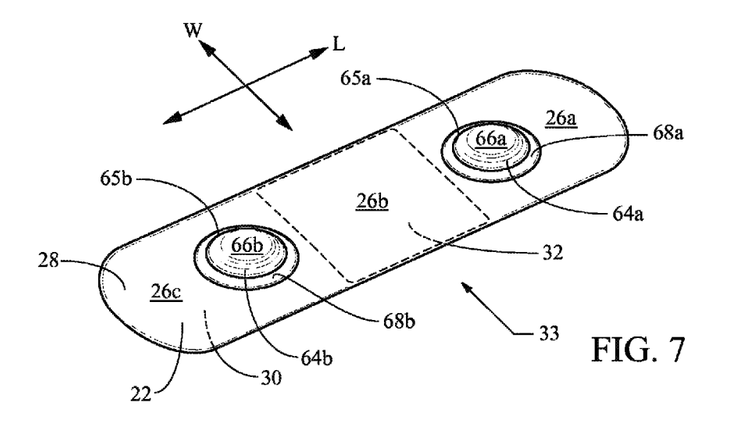
FIG. 7 is a perspective view of a seventh embodiment of a bandage with an adhesion reducing material contained in two selectively rupturable reservoirs attached to the bandage backing.

The selectively rupturable reservoirs of FIGS. 1-6 each include one or more linear reservoir segments. However, a variety of reservoir geometries may be used, both regular and irregular. Referring to FIG. 7, a seventh example of a bandage comprising a selectively releasable adhesion reducing material is depicted. In this example, bandage 33 comprises two selectively rupturable reservoirs 64a and 64b, each of which have a circular profile when viewed from a top plan view (i.e., orthogonally to the length L and width W axes of the backing layer 22). Selectively rupturable reservoirs 64a and 64b each include a corresponding housing 65a and 65b. Housing 65a comprises radially inward dome 66a and a radially outward flange 68a. Housing 65b comprises a radially inward dome 66b and a radially outward flange 68b.

Figure 9A:
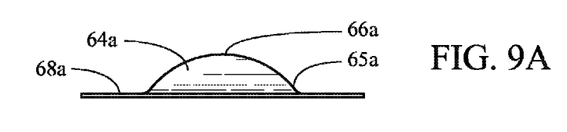
FIG. 9A is a side elevational view of one of the selectively rupturable reservoirs of the bandage of FIG. 7.

FIGS. 9A-9D are representative of selectively rupturable reservoir 64b although only reservoir 64a is specifically depicted. FIG. 9A provides a side elevational view of selectively rupturable reservoir 64a.

Figure 9B:
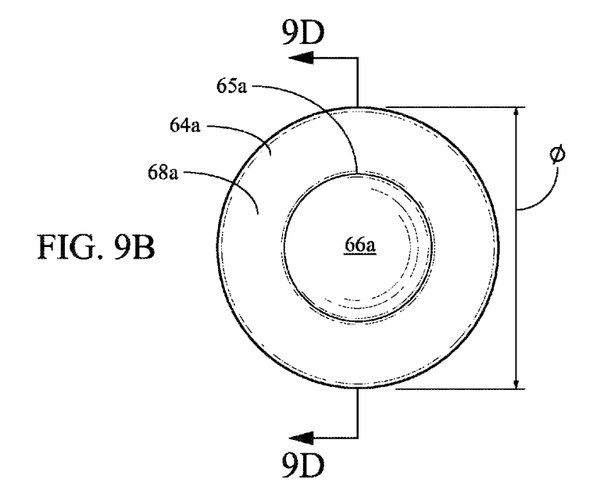
FIG. 9B is a top plan view of the reservoir of FIG. 9B.
Figure 9C:
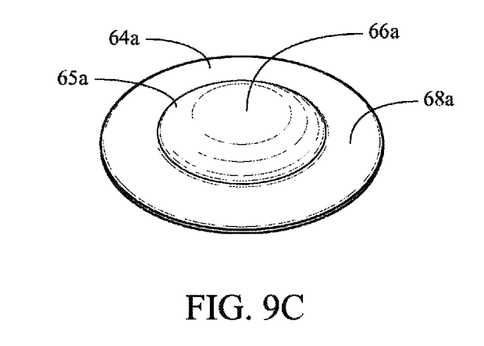
FIG. 9C is a perspective view of a the reservoir of FIG. 9A.
Figure 9D:
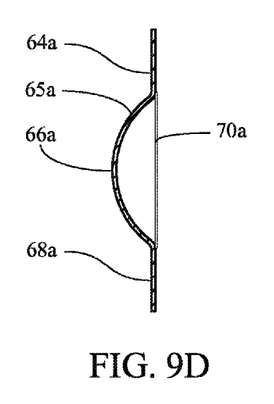
FIG. 9D is a side cross-sectional view taken along line 9D-9D of FIG. 9B.

FIG. 9B provides a top plan view of the selectively rupturable reservoir 64a, while FIG. 9c provides a perspective view of the reservoir 64a. A side cross-sectional view of selectively rupturable reservoir 64a is provided in FIG. 9D. As shown in FIG. 9D, the selectively rupturable reservoir 64a includes housing 65a and sealing membrane 70a. Together, housing 65a and sealing membrane 70a define an enclosed interior space that contains an adhesion reducing material of the type described previously. In FIG. 9D the adhesion reducing material is not shown. As with the previous examples of a selectively rupturable reservoir, the selectively rupturable reservoirs 64a and 64b are preferably self-contained, such that that the bandage backing does not define part of the reservoir. In contrast to structure in which a bandage backing defines part of a reservoir, self-contained reservoirs preferably reduce premature leakage or unintended release of the adhesion reducing material until bandage removal is desired.

In certain examples, the selectively rupturable reservoirs 64a and 64b of FIGS. 7-13 are configured to rupture differently than the selectively rupturable reservoirs of FIGS. 1-6. In accordance with such examples, the housings 65a and 65b are selectively depressible to cause their respective sealing membranes 70a and 70b to rupture and release the adhesion reducing material contained within them. In the example of FIG. 7, the domes 66a and 66b are depressible. In certain examples, the housings are formed of a depressible plastic. Exemplary plastics include polyethylenes, including without limitation LDPE, LLDPE, MDPE, HDPE, and UHMWDPE. The thickness and properties of the material used to form housings 65a and 65b and sealing membranes 70a and 70b are preferably selected such that depression of the housing domes 66a and 66b ruptures the corresponding sealing membranes 70a and 70b instead of the housings 65a and 65b themselves.

FIG. 10 provides an exploded cross-sectional view of a one implementation of selectively rupturable reservoir 64a and the backing layer 22 to which it is attached. In this implementation, a suitable housing adhesive 29 is applied across the upper surface 28 of backing layer 22 in a pattern that extends radially outward from the centerline of dome 66a to a portion or the edge of flange 68a. Suitable housing adhesives include cyanoacrylates, 2-octyl cyanoacrylate, and permanent acrylics. Suitable commercially available housing adhesives include Dymax® 222 Series cyanoacrylate, 3M Scotch-Weld Medical Grade cyanoacrylate/instant adhesive and 3M Scotch-Weld™ MG20 SF, 3M Scotch-Weld™ MG100 SF, 3M Scotch-Weld™ MG05 PR, 3M Scotch-Weld™ MG1500 PR, 3M Scotch-Weld™ MG05 LO, 3M Scotch-Weld™ MG100 LO, and 3M Scotch-Weld™ MG300 FLX, as well as Henkel's Loctite® 4011 Prism Instant Adhesive, Loctite® 4061 Prism Instant Adhesive, Loctite® 4014 Prism Instant Adhesive, and Loctite® 4035 Prism Instant Adhesive). Sealing membrane 70a is circular and extends from dome 66a centerline to a location that is radially outward of dome 66a and radially inward of the outer perimeter flange 68a. The housing 65a is affixed to bandage backing upper surface 28 such that the flange 68a bonds to the housing adhesive 29 coated on backing upper surface 28, thereby sandwiching a portion of outer periphery of sealing membrane 70a between flange 68a and backing layer 22 upper surface 28. In addition, the sealing membrane 70a bonds to the housing adhesive 29 located along the backing layer 22 upper surface 28 radially inward of flange 68a. Adhesion reducing material 72a is thus contained between the inner surface of dome 66a and sealing membrane 70a and isolated from backing layer 22 until being selectively released by the wearer.

In certain examples, the housing adhesive 29 is selected so as not to degrade or lose its adhesion when contacted by adhesion reducing material 72a. In accordance with such examples, the adhesion reducing material 72a selectively and preferentially reduces the skin adhesion of the skin adhesive coated on backing side 30 relative to the adhesion of the housing adhesive 29 to the backing layer 22 and flange 68a. The use of an adhesion reducing material that is formulated in this manner better ensures that the selectively rupturable reservoir 64a will remain intact while still reducing the adhesion of the skin adhesive to the wearer's skin.

The housing adhesive 29 may be applied in patterns other than the one illustrated in FIG. 10. Referring to FIG. 13, the housing adhesive 29 is applied in an annular pattern, such that the lower side (facing backing upper surface 28) of sealing membrane 70a does not contact the housing adhesive 29. In this example, flange 68a and upper surface 28 of backing layer 22 are adhesively attached by the annular pattern of housing adhesive 29. An outer annular portion of sealing membrane 70a is sandwiched between flange 68a and backing layer 22 upper surface 28 to hold the sealing membrane 70a in place within reservoir 64a. The annular pattern of FIG. 13 advantageously avoids contact between the housing adhesive 29 and the sealing membrane 70a which may impede the rupturing of the sealing membrane 70a when desired. In another example, the sealing membrane 70a is provided as a double-sided adhesive film of the type described previously. The double-sided adhesive film is cut to the desired membrane 70a geometry and dimensions and then applied to the backing layer 22. The backing layer 22 with the applied membrane 70a is then placed over reservoirs 64a (after filling them with the adhesion reducing material 72a). Commercially-available double-sided adhesive tapes of the type described previously may be used to provide the double sided adhesive film. FIGS. 10 and 13 show the membrane film 70a separate from the housing adhesive 29. However, when double-sided adhesive films are used, the membrane film 70a and adhesive 29 would be provided as an integral composite structure which is then adhered to backing layer 22 and the flange 68a. In certain preferred examples, if a double-sided adhesive film is used to form sealing membrane 70a, the membrane 70a will extend radially at least as far as the outer perimeter of the reservoir flange 68a so that the entire flange 68a is securely adhered to the membrane 70a.

In addition or as an alternative to the use of housing adhesive 29, the housing 65a may be heated and pressed against backing layer 22 to cause the housing 65a material to bond to the backing layer 22 material.

Figure 12:
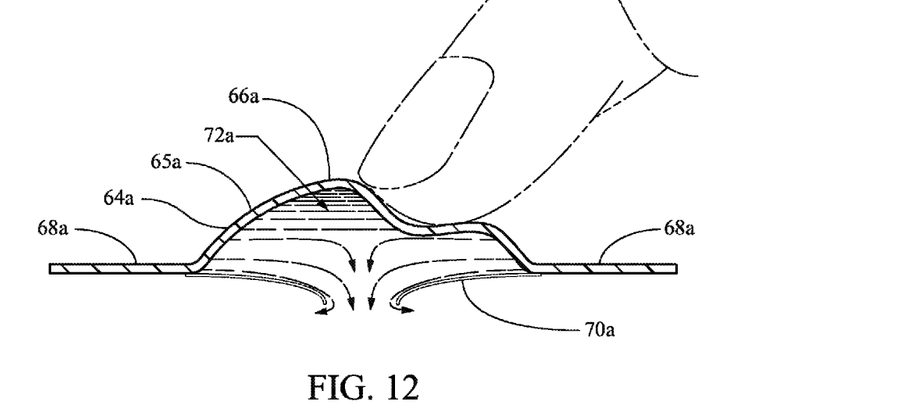
FIG. 12 is a side cross-sectional view of the reservoir of FIG. 10 in a ruptured configuration.

The use of bandage 33 (FIG. 7) comprising selectively rupturable reservoirs 64a and 64b will now be illustrated with reference to FIGS. 11 and 12. Bandage 33 is adhered to a wearer's arm with absorbent pad 32 placed in contact with a skin trauma, such as a wound, scrape, ulcer, etc. and the skin adhesive located in skin adhesive regions 26a and 26c on lower backing surface 30 in contact with the wearer's skin, on either side of the skin trauma. At this point, when viewed in cross-section, the selectively rupturable reservoir 64a is in a sealed condition as depicted in FIG. 11, with the adhesion reducing material securely contained within the enclosed space defined between the inner surface of housing dome 66a and sealing membrane 70a.

After a period of use the wearer decides to remove the bandage 33 from his or her skin. The wearer selects one of the selectively rupturable reservoirs 64a and 64b to use first. In this example, reservoir 64a is selected. As shown in FIG. 12 the wearer then depresses housing dome 66a with one of his or her fingers. Because the housing 65a contains the adhesion reducing fluid, the depressive force applied to dome 66a will cause the adhesion reducing material to apply a force to the sealing membrane 70a. As shown in FIG. 12, the sealing membrane 70a ruptures in response to the applied force, thereby providing a pathway for the adhesion reducing material 72a to migrate through backing layer 22 from upper surface 28 to lower surface 30 (which is coated with a skin adhesive). The interaction of the adhesion reducing material 72a and the skin adhesive reduces the adhesive forces between lower backing surface 30 and the wearer's skin, which allows the wearer to peel the portion of backing layer 22 within skin adhesive region 26a.

In certain examples, and depending on the viscosity of the adhesion reducing material 72a, the depression of the dome 66a will cause adhesion reducing material 72a to be squeezed out radially from the ruptured reservoir 64a, causing it to migrate from the lower surface 30 to the upper surface 28 of backing layer 22. The wearer can then spread the adhesion reducing fluid across the skin adhesive regions 26a of backing upper surface 28, allowing it to migrate back through backing layer 22 to lower backing surface 30 where it contacts a fuller area of the skin adhesive in the bandage's skin adhesive region 26a. The wearer can then repeat the process for selectively rupturable reservoir 64b to reduce the adhesion between the skin adhesive in skin adhesive region 26c of backing layer 22 and the wearer's skin. After giving the adhesion reducing material 72a and 72b (not shown) sufficient time to weaken the adhesive forces of the skin adhesive, the wearer can grip an end of backing layer 22 and peel off the bandage 33.

A method of making the bandage 33 of FIGS. 7 and 10-13 will now be described. In accordance with a first exemplary method, sheets of material used to form backing layer 22 are provided and are coated with a skin adhesive on one side (the side corresponding to backing layer 22 lower surface 30 in FIGS. 10 and 13). The backing layer material is then cut into strips and the absorbent material used to form absorbent pads 32 (not shown in FIGS. 7-13) is cut into strips. Using standard bandage making machinery, the absorbent pad material strips are adhesively adhered to a central portion of the strips of backing layer 22 material such that there is a portion of backing on either side of the absorbent pad strips. The portions of the backing strips on either side of the absorbent pad strips will ultimately be the first skin adhesive region 26a and the second skin adhesive region 26c.

The material used to form the housing 65a, 65b of the selectively rupturable reservoirs 64a, 64b (e.g., an LDPE material) is shaped using heat (such as heat rollers that form dimples) and/or pressure and cut to create a cross-sectional profile such as that of housing 65a in FIGS. 10 and 11 and the desired top plan view profile (e.g., FIG. 9B). The housings 65a and 65b are then filled with the adhesion reducing material 72a, 72b and strips of the sealing membrane material used to form sealing membranes 70a and 70b are placed over the open face of the housings 65a, 65b. The strips of backing material used to form backing layer 22 are then coated with an housing adhesive in the desired pattern (e.g., the circular pattern of housing adhesive 29 in FIG. 10 or the annular pattern of adhesive 31 in FIG. 13), and the housings 65a, 65b, sealing membrane strips, and backing strips are assembled together such that the housing is adhesively attached to the backing strips and a portion of the periphery of the sealing membrane is sandwiched between the periphery of the housing and the bandage backing, as best seen in FIGS. 10-13. The assembled bandage is then cut to the desired shape (e.g., the shape of FIG. 7). Release liner(s) with a suitable release coating are placed over the skin adhesive (not shown) on backing side 30, and the bandages are packaged and sterilized. In certain examples, form fill seal equipment or equivalent tooling is used to fill and seal the reservoirs 64a and 64b.

In addition to the foregoing method, an alternate method of making the bandage 33 may be used in which the material used to make sealing membrane 70a is provided as a bulk double-sided adhesive film (i.e., a film with an adhesive coating on both sides). The commercially available double sided adhesive tapes described previously may be provided. In one example, the double sided adhesive tape is cut into the desired size and shape of the sealing membranes 70a and 70b and applied to the backing material strips, on the side opposite the side on which the absorbent pad material is disposed. After filling the housings 65a and 65b with adhesion reducing material 72a and 72b, the composite strips of double sided adhesive film, backing material and absorbent pad are secured over the filled housings and the final bandages are cut to the desired shape and size.

Figure 8:
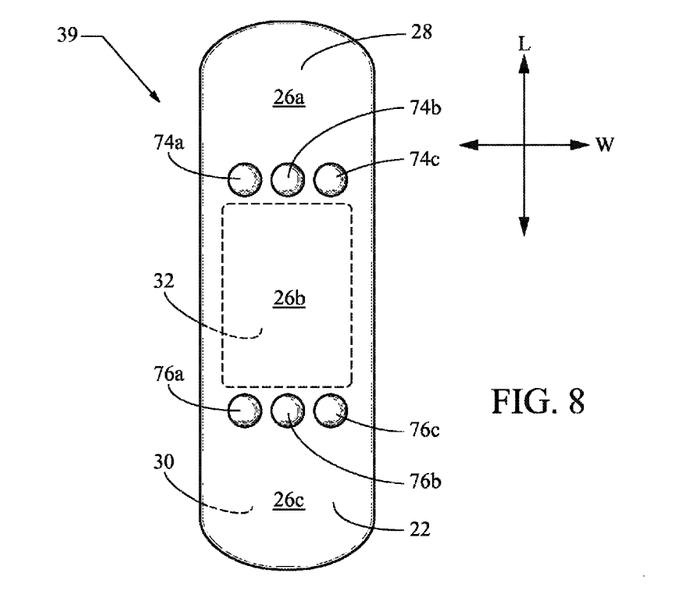
FIG. 8 is top plan view of an eighth embodiment of a bandage with an adhesion reducing material contained in six selectively rupturable reservoirs attached to the bandage backing.

Referring to FIG. 8, a modified version of bandage 33 of FIG. 7 is shown. Bandage 39 includes the same backing, skin adhesive, and absorbent pad structure of the bandage 33 of FIG. 7. However, it also includes six (6) selectively rupturable reservoirs 74a-c and 76a-c. Each selectively rupturable reservoir 74a-c and 76a-c has the same structure as selectively rupturable reservoirs 64a and 64b of FIG. 7. However, reservoirs 74a-c are aligned at a common position along the length axis direction L of the backing layer 22 and are spaced apart from one another along with width axis direction W of the backing layer 22. Correspondingly, selectively rupturable reservoirs 76a-c are aligned at a common position along the length axis direction L of the backing layer 22 and are spaced apart from one another along the width axis direction W of the backing layer 22. The first plurality of selectively rupturable reservoirs 74a-c is spaced apart from the second plurality of selectively rupturable reservoirs 76a-c along the length axis direction L of the backing layer 22. The total amount of adhesion reducing material held in all six (6) selectively rupturable reservoirs 74a-c and 76a-c per unit surface area of backing layer 22 upper surface 28 lying in the skin adhesive regions 26a and 26c is preferably the same as described above for the embodiment to of FIG. 7. In certain examples, the total amount of adhesion reducing material is substantially equally allocated among all six (6) selectively rupturable reservoirs 74a-c and 76a-c.

As indicated previously, the cross-sectional profiles of the selectively rupturable reservoirs 24, 38, 40, 48, 44a, 44b, 56, and 58 of FIGS. 1-6 preferably conform to the cross-sectional profile of the reservoir 64a shown in FIGS. 10-13 when viewed along a direction parallel to the length of the particular reservoir or linear reservoir segment, even though they would not appear circular when viewed in a top plan view. In addition, the housings and sealing membranes used in selectively rupturable reservoirs 24, 38, 40, 48, 44a, 44b, 56, and 58 of FIGS. 1-6 may be constructed and configured in a similar fashion as described for reservoirs 64a and 64b. Of course, instead of having a single flange 68a, the reservoirs 24, 38, 40, 48, 44a, 44b, 56, would have two flanges projecting in opposite directions away from one another in a direction that is transverse to the length of the particular reservoir or reservoir segment that includes the flanges. In addition, the housings used in reservoirs 24, 38, 40, 48, 44a, 44b, 56, and 58 may preferably be configured so as not to be depressible, but instead, to rupture when the corresponding pull tab is pulled. However, in certain examples, the reservoirs of FIGS. 1-6 could be configured without a pull tab or string and with selectively depressible housings that function in the same way that housings 65a and 65b function, i.e., such that depression of the housing ruptures the sealing membrane.

Figure 14:
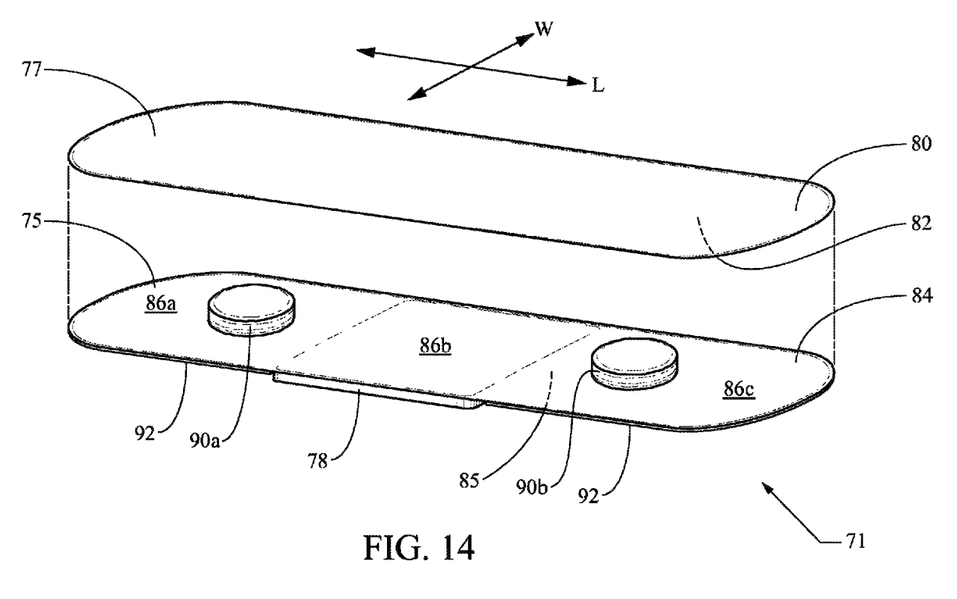
FIG. 14 is an exploded perspective view of ninth embodiment of a bandage with an adhesion reducing material contained in two deformable adhesion reducing material matrices from which the material is selectively releasable.

Referring to FIG. 14, another example of a bandage comprising a selectively releasable adhesion reducing material is provided. In this example, the bandage 71 includes at least one backing layer, a skin adhesive, and an adhesion reducing material layer, such that the at least one backing layer is located between the adhesion reducing material layer and the skin adhesive. In the particular example of FIG. 14, the at least one backing layer includes a second backing layer such that the adhesion reducing material layer is sandwiched between the second backing layer and the first backing layer.

Bandage 71 comprises a first backing layer 75 and a second backing layer 77. Backing layers 75 and 77 may be formed from the same materials described previously with respect to backing layer 22 of the previous embodiments. However, in certain examples, backing layers 75 and 77 are preferably formed polymeric films. In certain examples, the polymeric film is a polyethylene such s LDPE, LLDPE, MDPE, HDPE, UHMWPE. The polymeric films comprising backing layers 75 and 77 may comprise the same or different materials. However, they are preferably heat sealable to one another at their respective edges. In certain examples, the second backing layer 77 has a thinner profile than first backing layer 75 to provide greater adhesion reducing material layer actuation sensitivity. Other suitable polymeric films include those described previously with respect to backing 22 and/or sealing membrane 70a. At least the first backing layer 75 is preferably permeable to the adhesion reducing material, and in certain examples, both backing layers 75 and 77 are permeable to the adhesion reducing material.

First backing layer 75 includes an upper surface 84 and a lower surface 85. Backing layer 75 lower surface 85 comprises an absorbent pad 78 of the type described previously and a skin adhesive 92 separated into two sections along the length axis direction L of the first backing layer 75 by the absorbent pad 78.

Upper surface 84 of lower backing layer 75 is connected to an adhesion reducing material layer which comprises a first adhesion reducing material section 90a and a second adhesion reducing material layer section 90b. First adhesion reducing material section 90a is spaced apart from second adhesion reducing material section 90b in a direction along the length axis direction L of lower backing layer 75. In certain preferred examples, each adhesion reducing material layer section 90a and 90b is symmetrically disposed about the longitudinal midline of backing layer 75 (i.e., with its center at ½ of the backing layer 75 width dimension in the width axis direction W). First adhesion reducing material section 90a is located in the first skin adhesive section 86a of lower backing layer 75, while second adhesion reducing material layer section 90b is located in the second skin adhesive section 86c of lower backing layer 75. The first and second skin adhesive sections 86a and 86c are separated from one another by absorbent pad section 86b.

Each adhesion reducing material layer section 90a and 90b comprises a synthetic or natural matrix impregnated with an adhesion reducing material and which is capable of retaining the adhesion reducing material until deformed by a bandage wearer. The deformation of the adhesion reducing material section 90a and 90b causes the adhesion reducing material to be released from the corresponding matrix, whereupon it can migrate through lower backing layer 75.

The synthetic or natural matrices comprising each of the adhesion reducing material layer sections 90a and 90b may comprise films, foams, woven or non-woven fabrics, or gauzes formed from synthetic and/or natural materials. In certain examples, the synthetic or natural matrices are resilient such that they remain in an undeformed configuration until a deforming force is applied and then return to the undeformed configuration when the deforming force is removed. Suitable films include medical grade absorbent films such as MEDCO 8106 absorbent pads with a porous polyethylene covering, and 3M Tegaderm pad/film dressing with a non-adherent pad. Suitable foams include medical grade absorbent films such as flexible open cell polyurethane foams, re-bonded polyurethane foams, reticulated polyurethane filtration foams, expanded closed cell polyethylene foams, expanded closed cell crosslinked polyethylene foams, expanded EVA foams, expanded closed cell polystyrene foams, anti-static, conductive, flocked and melamine foams, flame laminated coated foams (tuftane, velcro fabric, aluminized mylar), closed cell neoprene & neoprene blend cellular materials, sponge rubbers (open and closed cell), and soft silicone. Suitable commercially available foams include Kendall® AMD foam dressing (Tyco Healthcare) and Mepilex® Absorbent Foam Dressing (Molnlycke Health Care). Suitable gauzes include Invacare® Lodoform gauze packing strips and Kendall Vaseline® Petrolatum Gauze (Tyco Healthcare). The adhesion reducing material layer sections may have a number of shapes and sizes. In the example of FIG. 14, they comprise a synthetic or natural matrix material cut into a generally cylindrical shape. The adhesion reducing material layer may comprise one or more adhesion reducing material layer sections. In the case of plural adhesion reducing material layer sections (as shown in FIG. 14), they may be spaced apart along the length axis L direction and/or the width axis W direction as desired. In addition to using discrete and separate adhesion reducing material layer sections, a single integral layer comprising a synthetic or natural deformable matrix impregnated with an adhesion reducing material may also be used.

In one example, the first and second backing layers 75 and 77 are bonded together to retain the first and section adhesion reducing material layer sections 90a and 90b between the backing layers 75 and 77. Bonding techniques such as heat sealing or adhesives may be used to hold the backing layers 75 and 77 together.

In certain examples, the first adhesion reducing material section 90a and second adhesion reducing material layer section 90b are affixed to the upper surface 84 of lower backing layer 75 by a suitable adhesive, preferably one that is not sensitive to contact with and which will not degrade when contacted by the adhesion reducing material. In other examples, the bonding of the first and second backing layers 75 and 77 is carried out in a way to securely hold the first and second adhesion reducing material layer sections 90a and 90b in place.

In additional examples, the lower backing layer 75 is formed with recesses (not shown), such as cavities or dimples, that are complementarily sized to receive a portion of a respective one of the first and second adhesion reducing material layer sections 90a and 90b. In such examples, the first and second adhesion reducing material layer sections 90a and 90b are preferably not completely enclosed in the corresponding recesses but instead include a portion that projects away from lower backing layer 75 upper surface 84 to facilitate deformation by the user when desired.

In certain implementations, an adhesive may be applied to the interior of the recesses to more securely hold the adhesion reducing material layer sections 90a and 90b in place. One advantage to using a recessed design is that in some instances the overall thickness profile (i.e., the thickness in a direction orthogonal to the length axis direction L and width axis direction W) can be reduced relative to designs in which the adhesion reducing material layer sections 90a and 90b are connected to the lower backing layer 75 surface at a point of contact that is flush with the remainder of the lower backing layer 75. In certain preferred examples in which such recesses are employed, the upper backing layer 77 is bonded to the lower backing layer 75 using techniques such as heat sealing or adhesive bonding to further secure the adhesion reducing material layer sections 90a and 90b.

In certain cases—especially those in which the adhesion reducing material layer sections 90a and 90b are held in recesses formed in lower backing layer 75—it may be desirable to print markings, graphic, or other indicia on the upper backing layer 77 immediately over the adhesion reducing material layer sections 90a and 90b so a bandage wearer can more accurately direct a deformation force to the sections 90a and 90b to release the adhesion reducing material.

Bandage 71 will typically be applied to the wearer's body with absorbent pad 78 in contact with a skin trauma and skin adhesive 92 in contact with portions of the wearer's skin adjacent the skin trauma. When the wearer wishes to remove the bandage 71, he or she will depress the upper backing layer 77 at a position along the length L and width W direction that corresponds to the location of the adhesion reducing material layer sections 90*a* and 90*b* along the length L and width direction W. The depression of upper backing layer 77 will cause the corresponding adhesion reducing material section 90*a* and 90*b* to deform, thereby releasing the adhesion reducing material from its synthetic or natural matrix. The released adhesion reducing material then migrates through the lower backing layer 75 to contact the skin adhesive 92 and reduce its adhesive force on the wearer's skin.

In certain examples wherein upper backing layer 77 is permeable to the adhesion reducing material, the adhesion reducing material may squeeze out away from the position of the adhesion reducing material layer sections 90*a* and 90*b* and migrate to the upper surface 80 of upper backing layer 77 laterally of the adhesion reducing material layer sections 90*a* and 90*b*, allowing the user to spread the adhesion reducing material over the upper surface 80 of upper backing layer 77 in first skin adhesive section 86*a* and second skin adhesive region 86*c*. Spreading of the adhesion reducing material in this manner allows the material to then migrate through the upper backing layer 77 and lower backing layer 75 and increases the area of contact between the skin adhesive 92 and the adhesion reducing material. After selectively releasing the adhesion reducing material from adhesion reducing material layer sections 90*a* and 90*b* in this manner, the user can then peel the bandage from his or her skin.

In those examples in which the adhesion reducing material layer sections 90*a* and 90*b* are held in recesses formed in first backing layer 75, it would be possible to simply load the adhesion reducing material in the recesses and then seal the lower backing layer 75 with the upper backing layer 77, thereby avoiding the need for the adhesion reducing material layer sections 90*a* and 90*b* altogether. The wearer could then rupture the recesses to release the adhesion reducing material. However, the use of first deformable synthetic or natural matrices as the sections 90*a* and 90*b* achieves several advantages over such a design. For example, if the adhesion reducing material were provided in backing layer recesses, the first backing layer 75 would likely have to be occlusive (non-permeable) to the adhesion reducing material to prevent leakage. Upper backing layer 77 would similarly have to be occlusive to prevent the fluid from leaking from the recesses through upper backing layer 77. In addition, the adhesion reducing material could tend to leak out of the bandage from between the two backing layers 75 and 77. Because the deformable synthetic or natural matrices allow for the use of permeable backing layers 75 and 77, the released adhesion reducing material can be squeezed back through the backing layers 75 and 77, allowing the wearer to spread it over the surface area of upper backing layer 77 in the skin adhesive sections 86*a* and 86*c*, causing the material to migrate back through the backing layers 77 and 75 to the skin adhesive 92 and thereby providing a greater contact surface area between the adhesion reducing material and the skin adhesive 92.

In certain examples, the amount of adhesion reducing material held in the first and second adhesion reducing material sections 90*a* and 90*b* is related to or proportional to the surface area of the lower backing layer 75 lying within the skin adhesive sections 86*a* and 86*c*. In certain examples, the volume per unit surface area of skin adhesive sections 86*a* and 86*c* on lower backing layer upper surface 84 is preferably at least about 1.2 $\mu$l/cm$^2$, more preferably at least about 1.8 $\mu$l/cm$^2$, and still more preferably at least about 2.0 $\mu$l/cm$^2$. At the same time or in other examples, the volume per unit surface area is preferably not more than about 4.6 $\mu$l/cm$^2$, more preferably not more than about 3.4 $\mu$l/cm$^2$, and still more preferably not more than about 2.5 $\mu$l/cm$^2$. In one example, the volume of adhesion reducing material per unit surface area of lower backing layer upper surface 84 in the skin adhesive regions 26*a* and 26*c* is about 2.3 $\mu$l/cm$^2$.

A method of using the bandage 71 will now be described. To protect a skin trauma, the user first removes a release liner (not shown) from lower backing layer 75 lower side 85 which covers the skin adhesive 92 and absorbent pad 78 as in the case of a standard bandage. The absorbent pad 78 is then placed in contact with the skin trauma to protect it and absorb any fluids associated with it. The portions of lower surface 85 of first backing layer 75 lying within the skin adhesive sections 86*a* and 86*c* are then placed in contact with the skin on either side of the skin trauma to affix the bandage to the wearer.

After a desired period of use, the wearer then removes the bandage by depressing the upper backing layer 77 at first location along the length and width axis directions that is aligned with a first selected one of the adhesion reducing material layer sections 90*a* or 90*b*. The depression of the upper backing layer causes the first and second adhesion reducing material layer sections 90*a* or 90*b* to release the adhesion reducing material. The adhesion reducing material travels across the upper surface 84 of lower backing layer 75 and then penetrates the lower backing layer 75 to come into contact with skin adhesive 92 on lower surface 85 of lower backing layer 75. In certain examples, the points of attachment between the adhesion reducing material layer sections 90*a* and 90*b* and upper surface 84 of lower backing layer 75 are occluded to prevent premature leakage of the adhesion reducing material through the lower backing layer 87 at the points of attachment.

The wearer then selects a second one of the first and second adhesion reducing material sections 90*a* and 90*b* and depresses the upper backing layer 77 at a location that is aligned with the selected second one of the first and second adhesion reducing material sections 90*a* and 90*b*, causing the first and second adhesion reducing material layer sections 90*a* or 90*b* to release the adhesion reducing material.

If the lower backing layer 75 and upper backing layer 77 are permeable to the adhesion reducing material, some amount of it will likely penetrate the upper backing layer 77 following deformation of the adhesion reducing material layer sections 90*a* and 90*b*. The wearer can then use his or her fingers or a suitable instrument to spread the adhesion reducing material along the upper surface 80 of upper backing layer 77 to cover a desired portion of the upper surface 80 lying within the skin adhesive sections 86*a* and 86*c*. The adhesion reducing material will then penetrate back through the upper backing layer 77 and lower backing layer 75 to contact skin adhesive 92 and weaken its adhesion to the wearer's skin. The wearer can then grip the underside of the lower backing layer 75 and peel the bandage off of his or her skin.

A method of making the bandage 71 of FIG. 14 will now be described. In accordance with a first exemplary method, sheets of material used to form first backing layer 75 are provided and are coated with a skin adhesive 92 on one side. The backing layer material is then cut into strips and the absorbent material used to form absorbent pads 78 is cut into strips. Using standard bandage making machinery, the absorbent pad material strips are adhesively adhered to a central portion of the strips of backing layer 75 material such that there is a portion of backing on either side of the absorbent pad strips.

The combined backing/absorbent pad strips are then recessed on the side of the backing strips opposite the absorbent pad material. Impregnated first and second adhesion reducing material sections are adhesively attached in the recesses. In those examples where lower backing layer 75 is not recessed, the first and second adhesion reducing material sections are adhesive attached to the surface of the backing strips opposite the absorbent pad.

The material used to form upper backing layer 77 is formed into strips having a width similar to the width of the strips of lower backing layer 75 material. The upper backing layer material 77 is affixed to the lower backing material layer using adhesives, heat sealing and/or pressure thereby forming long strips of assembled bandage material which can then be cut width-wise to yield the final bandages. A release liner with a suitable release coating is placed over the skin adhesive 92 and absorbent pad 78, and the bandages are packaged and sterilized using known techniques, which are preferably selected so as not to degrade or cause the premature release of the absorbent reducing material from the first and second adhesion reducing material sections 90a and 90b.

The present invention has been described with reference to certain exemplary embodiments thereof. However, it will be readily apparent to those skilled in the art that it is possible to embody the invention in specific forms other than those of the exemplary embodiments described above. This may be done without departing from the spirit of the invention. The exemplary embodiments are merely illustrative and should not be considered restrictive in any way. The scope of the invention is defined by the appended claims and their equivalents, rather than by the preceding description.

What is claimed is:

1. A bandage, comprising:
   a first backing layer having a first side and a second side;
   a skin adhesive on the first backing layer first side;
   two adhesion reducing material matrices on the first backing layer second side, wherein the two adhesion reducing material matrices are impregnated with an adhesion reducing material and have a retaining configuration and a releasing configuration;
   a second backing layer having a first side and a second side, wherein the second backing layer first side faces the first backing layer second side; and
   an absorbent pad on the first backing layer first side, wherein the first backing layer includes an absorbent pad region, and the two adhesion reducing material matrices are located outside of the absorbent pad region.

2. The bandage of claim 1, wherein the adhesion reducing material comprises at least one selected from a liquid and a semi-solid.

3. The bandage of claim 2, wherein the adhesion reducing material comprises a plant extract.

4. The bandage of claim 2, wherein the adhesion reducing material comprises an animal extract.

5. The bandage of claim 2, wherein the adhesion reducing material comprises a petroleum extract.

6. The bandage of claim 2, wherein the adhesion reducing material comprises water.

7. A method of removing the bandage of claim 1, wherein the first backing layer skin adhesive is adhered to a wearer's skin, the method comprising:
   deforming the two adhesion reducing material matrices to release the adhesion reducing material; and
   peeling the first backing layer from the wearer's skin.

8. The method of claim 7, wherein deforming the two adhesion reducing material matrices comprises pressing the second backing layer.

9. The method of claim 7, wherein the bandage includes an absorbent pad on the first backing side such that when the skin adhesive is adhered to the wearer's skin, the absorbent pad is in contact with a skin trauma.

10. The bandage of claim 1, wherein the first backing layer is permeable to the adhesion reducing material.

11. The bandage of claim 10, wherein the second backing layer is permeable to the adhesion reducing material.

12. The bandage of claim 1, wherein the two adhesion reducing material matrices comprise one selected from a film, a foam, and a gauze, and when either of the two adhesion reducing material matrices is deformed from the retaining configuration to the releasing configuration, the adhesion reducing material is released from the deformed adhesion reducing material matrix.

13. The bandage of claim 1, wherein the two adhesion reducing material matrices are resilient.

14. The bandage of claim 1, wherein the first backing layer second side comprises two recesses, and each of the two adhesion reducing material matrices is disposed in one of the two recesses.

15. The bandage of claim 1, wherein at least a perimeter portion of the first backing layer is attached to at least a perimeter portion of the second backing layer.

16. The bandage of claim 1, wherein each of the two adhesion reducing material matrices projects away from the first backing layer second side.

* * * * *